United States Patent
Edinger et al.

(10) Patent No.: US 7,335,942 B2
(45) Date of Patent: Feb. 26, 2008

(54) FIELD EFFECT TRANSISTOR SENSOR

(75) Inventors: Klaus Edinger, Laurel, MD (US); Ivajlo Rangelow, Baunatal (DE); Piotr Grabiec, Warsaw (PL); John Melngailis, Chevy Chase, MD (US)

(73) Assignee: Universitaet Kassel, Kassel (DE)

( * ) Notice: Subject to any disclaimer, the term of this patent is extended or adjusted under 35 U.S.C. 154(b) by 0 days.

(21) Appl. No.: 10/495,632

(22) PCT Filed: Nov. 8, 2002

(86) PCT No.: PCT/EP02/21513

§ 371 (c)(1),
(2), (4) Date: Sep. 27, 2004

(87) PCT Pub. No.: WO03/042627

PCT Pub. Date: May 22, 2003

(65) Prior Publication Data

US 2005/0062116 A1    Mar. 24, 2005

(30) Foreign Application Priority Data

Nov. 14, 2001   (DE) ................ 101 55 930

(51) Int. Cl.
*H01L 29/72*   (2006.01)
(52) U.S. Cl. .............. 257/328; 257/24; 257/414; 257/401; 257/618; 257/623; 257/653
(58) Field of Classification Search ........... 257/328, 257/24, 401, 414, 618, 623, 653
See application file for complete search history.

(56) References Cited

U.S. PATENT DOCUMENTS

| 4,020,830 A | 5/1977 | Johnson et al. |
| 4,218,298 A | 8/1980 | Shimada et al. |
| 4,668,865 A | 5/1987 | Gimzewski et al. |
| 4,698,657 A | 10/1987 | Watanabe et al. |
| 4,873,871 A | 10/1989 | Bai et al. |

(Continued)

FOREIGN PATENT DOCUMENTS

| DE | 4115414 C2 | 7/1995 |
| EP | 0496672 A1 | 7/1992 |
| EP | 0984444 A2 | 3/2000 |

OTHER PUBLICATIONS

Bergveld, Piet; "Development, Operation, and Application of the Ion-Sensitive Field-Effect Transistor as a Tool for Electrophysiology"; 1972, *IEEE Transactions on Biomedical Engineering*, vol. BME-19, No. 5, pp. 340-351.

Jansen, Henri et al.; "A survey on the reactive ion etching of silicon in microtechnology"; 1996, *J. Micromech. Microeng.*, vol. 6, pp. 14-28.

Matsuo, Tadayuki et al.; "An Integrated Field-Effect Electrode for Biopotential Recording"; 1974, *IEEE Transactions on Biomedical Engineering*, pp. 485-487.

*Primary Examiner*—Edward Wojciechowicz
(74) *Attorney, Agent, or Firm*—Townsend and Townsend and Crew, LLP

(57) ABSTRACT

The invention relates to a sensor, especially for the probe of a screen probe microscope, for examining probe surfaces (40) or areas adjacent to the sensor, comprising at least one field effect transistor (FET) made of at least one semiconductor material. The invention also relates to a Hall sensor made of at least one semiconductor material for detecting magnetic fields and whose lateral resolution capacity can be electrically adjusted, in addition to a semiconductor electrode (28) whose electrode surface can be electrically adjusted.

9 Claims, 5 Drawing Sheets

U.S. PATENT DOCUMENTS

| | | |
|---|---|---|
| 4,881,109 A | 11/1989 | Ogawa |
| 4,960,722 A | 10/1990 | Ogawa |
| 5,225,771 A | 7/1993 | Leedy |
| 5,393,401 A | 2/1995 | Knoll |
| 5,546,375 A | 8/1996 | Shimada et al. |
| 5,578,814 A | 11/1996 | Dadali et al. |
| 6,477,132 B1 * | 11/2002 | Azuma et al. .............. 369/126 |
| 6,521,921 B2 * | 2/2003 | Lim et al. ................... 257/255 |
| 2001/0021575 A1 | 9/2001 | Furukawa et al. |
| 2002/0008304 A1 | 1/2002 | Lim et al. |

* cited by examiner (a)

(b)

(c)

(d)

FIELD EFFECT TRANSISTOR SENSOR

BACKGROUND OF THE INVENTION

The invention relates to a sensor with at least one field effect transistor (FET) having at least one semiconductor material.

The use of a field effect transistor, in particular of a metal oxide semiconductor field effect transistor (MOS-FET) as a sensor is known. Whereas, in a customary MOS-FET the electrical resistance of the transistor channel (gate) is controlled by means of a gate electrode insulated relative to the channel by an oxide layer an electrode of this kind is not provided in a FET sensor. In the use of the FET as a sensor the resistance of the transistor channel is influenced by the interaction with a sample to be investigated, whereby conclusions can be drawn relating to the nature of the sample, in particular the sample surface.

The use of a field effect transistor as an acceleration sensor is, for example, known from U.S. Pat. No. 4,873,871. In this connection a microbeam which can be deflected on acceleration of the sensor is arranged in the vicinity of the transistor channel such that when the microbeam approaches the transistor channel, or the microbeam is moved away from the transistor channel, the channel resistance correspondingly changes.

In U.S. Pat. No. 4,020,830 the use of a field effect transistor as a chemical sensor is disclosed. In this connection a membrane is applied onto an insulating layer of the transistor channel and is brought into contact with the surface of a sample to be investigated, for example a liquid. The membrane is designed such that it interacts selectively with a predetermined type of ions of the sample. The application of a voltage between the sample and the transistor results in an interaction between the membrane and the ions of the sample, which in turn leads to a change of the channel resistance of the transistor which allows conclusions to be drawn on the nature of the sample investigated.

SUMMARY OF THE INVENTION

It is an object of the invention to provide a field effect transistor for the investigation of sample surfaces with a spatial resolution which is as high as possible.

A sensor in accordance with the invention, in particular for a probe of a scanning probe microscope for the investigation of sample surface or fields adjacent to the sensor provides at least one field effect transistor (FET) having at least one semiconductor material without a gate electrode, the surface of which is three-dimensionally formed, at least in the region of the channel (gate).

The lateral resolution of an FET sensor depends both on the spacing of the sensor from the sample, which is essentially limited by the thickness of a layer of a dielectric covering the transistor channel, and also on the dimension of the channel, i.e. its length and its width. The smaller the sample/sensor spacing is selected to be and the smaller the channel is dimensioned the higher is the resolution capability of the sensor.

In this connection the dimension of the transistor channel is amongst other things pre-set by the method used for the manufacture of the FET sensor, in particular the lithography process. However, if the transistor surface is additionally of three-dimensional shape, for example pointed in the region of the channel, as provided by the invention, and if the channel is laid over the apex of a pyramid or a cone consisting of a semiconductor material, the lateral resolution capability can exceed the dimension of the channel, because of the dependence on distance of the electrical field strength, and can thus exceed the maximum resolution capability otherwise limited by the structuring process. The lateral resolution capability of a sensor in accordance with the invention is consequently increased relative to a sensor with a planar transistor surface through the three-dimensional formation of the transistor surface provided in accordance with the invention, at least in the region of the channel (gate).

A sensor in accordance with the invention can thus be particularly well used for the detection of electrical, magnetic and/or chemical interactions and also for the detection of electromagnetic radiation with high spatial resolution.

Since a peak geometry of this kind can also be used in detection probes in scanning force microscopes, a sensor in accordance with the invention can additionally be used simultaneously or at the same time as a probe of a customary scanning force microscope.

Advantageous embodiments of the invention can be found in the subordinate claims, the description and the drawing.

In accordance with an advantageous embodiment of the sensor of the invention the surface in the region of the channel (gate) is of pyramid-like shape. In this way the dependence and distance of the electrical field strength can be particularly well exploited to improve the resolution capability of the sensor. In addition pyramid-like structures, in particular in crystalline semiconductor substrates, can easily be generated by plasma etching processes (see for example H. Jansen et al., A Survey on the Reactive Ion Etching of Silicon in Microtechnology, J. Micromech., Microeng., Vol. 6, pages 14 and sequel (1996)).

Alternatively, the surface in the region of the channel (gate) can be of conical, step-like or wedge-like shape.

In accordance with one variant of the sensor of the invention the transistor is formed as a field effect transistor of the enhancement type (enhancement mode FET).

In accordance with a particularly preferred embodiment of the sensor of the invention the transistor is formed as a field effect transistor of the depletion type (depletion mode FET). In transistors of this kind a current flows between the source and the drain even without an external electrical field and represents a measure for the electrical resistance of the channel (gate). In contrast to the FET of the enhancement type the channel does not first have to be inverted by an external field in order to enable a current flow between source and drain, so that in the FET sensor of the depletion type, comparatively small electrical fields are sufficient in order to change the channel resistance and thus make them susceptible to the measurement. The use of a field effect transistor of the depletion type consequently results in a sensor with enhanced sensitivity.

It is particularly favorable when the sensor has an electrode for the application of a setting voltage in order to electrically pre-set the electrical resistance of the channel (gate). In this manner the sensitivity of the sensor in accordance with the invention can be matched to the strength of the electrical field.

The transistor is advantageously formed as a depletion layer field effect transistor junction field effect transistor JFET). Such transistors enable the setting of the channel resistance to a predetermined value in a simple manner.

Furthermore, a subject of the invention is a method for the spatially resolved investigation of a sample surface extending essentially in the XY-direction in which a sensor in accordance with one of the previously named kind is attached to an end of a probe of a scanning probe microscope pointing towards the sample surface, the sensor is brought into the vicinity of the sample surface, a voltage is applied between the source and drain of the transistor, a voltage is if necessary applied between the sample and the sensor, the sensor being moved in the XY-direction relative to the sample surface, in particular in a scanning movement, with either the sensor being kept at a constant level Z with respect to the XY-plane above the sample surface and the current flow being measured from the source through the channel to the drain and being recorded in dependence on the XY position of the sensor, or the sensor is moved at a constant spacing from the sample surface in such a way that the current flow from the source through the channel to the drain remains constant and the extent of a movement of the sensor in the Z-direction is recorded in dependence on the XY position of the sensor, and an image of the sample surface is produced from the recorded current values or deflection values.

The method of the invention represents a possibility for the use of a sensor in accordance with the invention in which the resolution capability of the sensor can be particularly well exploited.

An FET sensor of the depletion type is preferably used and a setting voltage is applied to the sensor in order to set the resistance of the channel (gate) to a predetermined value. In this way the sensitivity of the sensor can be matched to the sample to be investigated.

A further subject of the invention is a Hall sensor consisting of at least one semiconductor material for the detection of magnetic fields, with the lateral resolution capability of the Hall sensor being capable of being set electrically. By means of a Hall sensor of this kind the strength in a magnetic field can be measured with a particularly good spatial resolution.

In a Hall sensor in accordance with the invention there are preferably at least two crossing channels provided transversely to one another, in particular standing at right angles to one another, in a substrate in a crossing region, the channels having a reversed polarity of the majority charge carriers in comparison with the substrate, wherein a control voltage can be applied to one channel to generate a current flow through the channel and a Hall voltage produced by a magnetic field can be measured at the other channel.

A Hall sensor in accordance with the invention advantageously has an electrode for the application of a setting voltage in order to set the extent of the crossing region in the plane spanned by the channels. In this manner the resolution capability of the Hall sensor can be set and can in particular be increased.

A further subject of the invention is a semiconductor electrode, the electrode area of which can be set electrically set. By means of an electrode of this kind capacity measurements with particularly high spatial resolution or electrochemical potential determinations can be carried out on samples to be investigated.

In a semiconductor electrode in accordance with the invention a first channel section is advantageously provided extending substantially parallel to the substrate surface in a semiconductor substrate and can be contacted from outside of the substrate, with the first channel section merging into a second channel section extending perpendicular to the substrate surface and bordering on the substrate surface, with the electrode area being determined by the lateral extent of the second channel section at the substrate surface.

The channel sections preferably have a polarity of the majority charge carriers which is reversed relative to the substrate.

It is particularly favorable when the semiconductor electrode has an electrode for the application of a setting voltage in order to set the extent of the channel sections, and in particular the extent of the setting channel section at the substrate surface. In this way, the electrode area can be set, and can in particular be reduced, whereby the resolution of a spatially resolved capacity measurement or potential determination can be set, and can in particular be increased.

A further subject of the invention is a method for the spatially resolved capacity measurement or electrochemical potential determination of a sample extending in the XY direction in which a semiconductor electrode in accordance with one of the above named kinds is attached to an end of a sample of a scanning probe microscope pointing to the sample surface, a setting voltage is applied to the semiconductor substrate in order to set the extent of the electrode area to a predetermined value, the electrode is moved in the XY direction relative to the sample, in particular in a scanning movement, the electrode is brought into contact with the sample at predetermined intervals, wherein a voltage is applied if necessary between the sample and the sensor, the capacity or the electrochemical potential of the sample is determined and is recorded in dependence on the XY position of the electrode, and an image of the sample is produced from the recorded capacity values or potential values.

In the following the various aspects of the invention will be described purely by way of example in each case with respect to an embodiment and with reference to the drawing.

DESCRIPTION OF THE PREFERRED EMBODIMENTS

Figure 1:
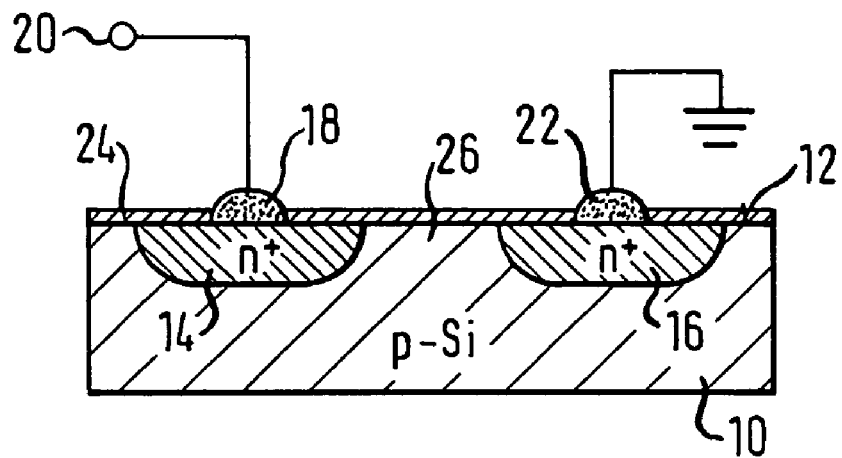
FIG. 1 a field effect transistor of the enhancement type without gate electrodes.

In FIG. 1 a known planar field effect transistor (FET) of the enhancement type (enhancement mode FET) is shown which can be used as a detector and which includes a p-doped silicon substrate 10. In the vicinity of one sensor surface 12 the substrate 10 has two regions 14, 16, which are each $n^+$-doped, the one region 14 being contacted by means of a drain electrode 18, being connected to a voltage source 20 and acting as a drain. The other $n^+$-doped region 16 is earthed by means of a source electrode 22 and acts as a source. The sensor surface 12 is provided with a layer 24 of a dielectric, preferably of silicon dioxide.

The region close to the surface of the substrate 10 disposed between drain 14 and source 16 forms the channel 26 (gate) of the transistor. Whereas a gate electrode is typically provided on the oxide layer 24 in the region of the channel 26 in order to control the conductivity of the channel 26 and thus the current flow from the source 16 to the drain 14 by means of a voltage applied to the gate electrode in metal oxide semiconductor field effect transistors (MOSFET), a gate electrode of this kind is not provided in an FET used as a sensor. With sensor transistors of this kind, the influencing of the conductivity of the channel takes place by electrical, magnetic or chemical interactions of the channel 26 with the external fields or sample surfaces to be investigated, or by exposing the sensor surface 12 to electromagnetic radiation.

The sensor shown in FIG. 1 is an FET of the enhancement type, which signifies that the channel 26 has basically the same doping as the substrate 10. A current flow from the source 16 to the drain 14 can thus only take place when the channel 26 is inverted, i.e. when an external electrical field to be investigated is so strong that the electrical resistance of the channel 26 is adequately reduced by the generation of a sufficient number of mobile charge carriers (electrons).

Since correspondingly strong electrical fields are required for the inversion of the channel 26 an FET of the enhancement type has a relatively low sensor sensitivity. In addition the channel 26 must be inverted over its entire length in order to achieve a current flow from the source 16 to the drain 14. Since the resolution capability of a sensor of this kind is determined also by the dimension of the channel 26 in addition to the thickness of the oxide layer 24, the resolution capability of the sensor shown in FIG. 1 is restricted by the spacing between drain 14 and source 16, i.e. it cannot be better than the length of the channel 26.

Figure 2:
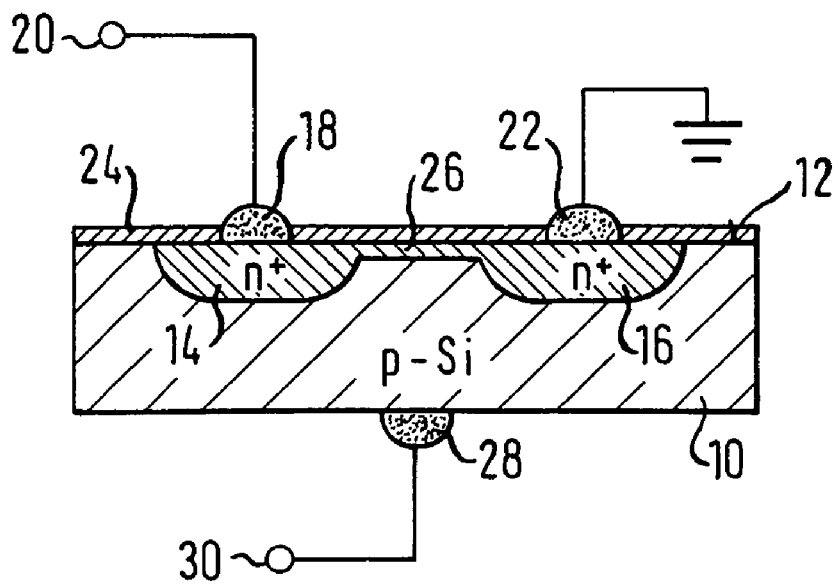
FIG. 2 a depletion layer field effect transistor of the depletion type without gate electrode.

In FIG. 2 a sensor of the type of a depletion layer field effect transistor (junction field effect transistor JFET) of the depletion type is shown with a planar sensor surface 12. In contrast to the FET of the enhancement type the channel 26 of an FET of the depletion type has a doping of the same type as the drain 14 and source 16—in the illustrated example an n-doping. The system channel 26/substrate 10 consequently forms a pn junction.

The channel 26 is already conductive in a starting state so that when applying a voltage between drain 14 and source 16 a current flows even without the interaction of the sensor with an external electric field. In this manner weaker electric fields can be measured so that an FET of the depletion type has a higher sensor sensitivity than an FET of the enhancement type. At the same time a higher resolution capability of a sensor can be achieved since it is not necessary for the whole channel 26 to be inverted for a current flow between source 16 and drain 14. The resolution is basically therefore not restricted by the length of the channel 26.

In addition the substrate 10 of a JFET is contacted by a setting electrode 28 which is connected to a voltage source 30 in order to apply a setting voltage between substrate 10 and channel 26. Through the setting voltage the extent of the channel 26 in a direction perpendicular to the sensor surface 12, i.e. the depth of the channel 26 can be varied. By applying the voltage in the blocking direction of the pn junction the cross-section of the channel 26 can be reduced by depletion of charge carriers.

One consequently obtains through the setting voltage an additional possibility of pre-setting the conductivity of the channel 26 and thus of matching the sensitivity of the sensor to the strength of an electrical field which is to be investigated.

Figure 3:
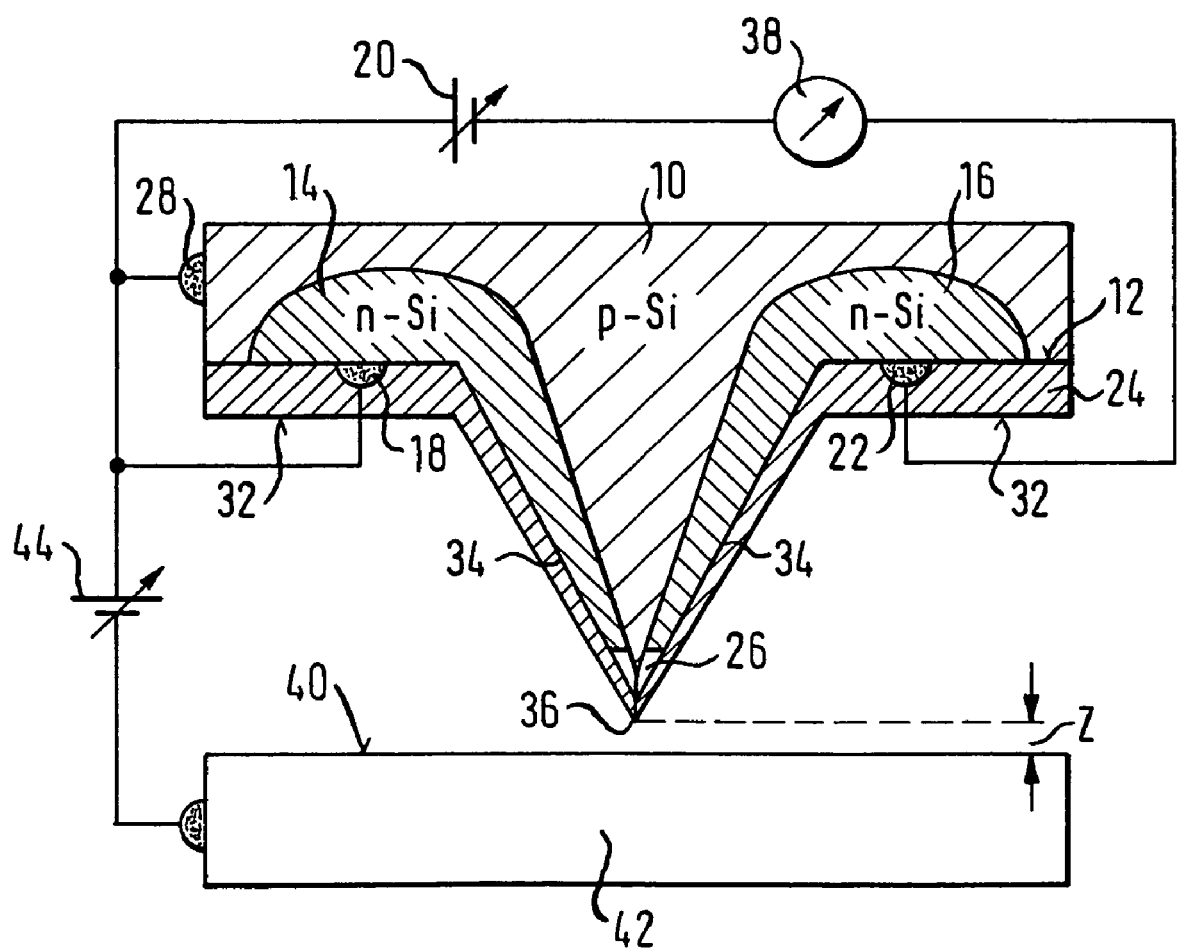
FIG. 3 a sensor in accordance with the invention.
Figure 4:
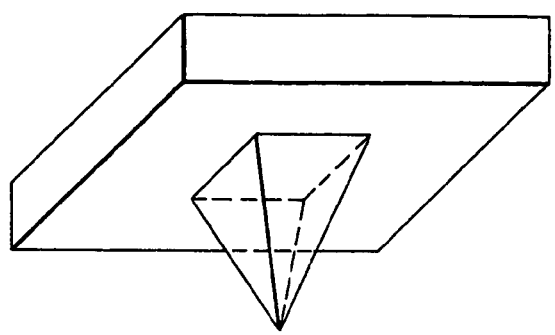
FIG. 4 alternative designs of the sensor surface in the region of the channel.
Figure 4:
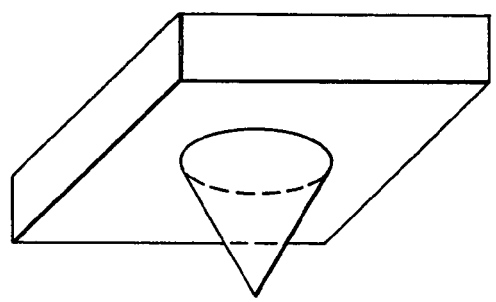
Figure 4:
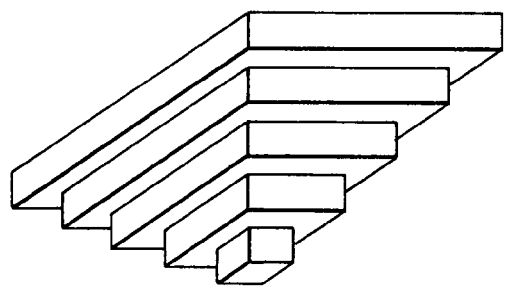
Figure 4:
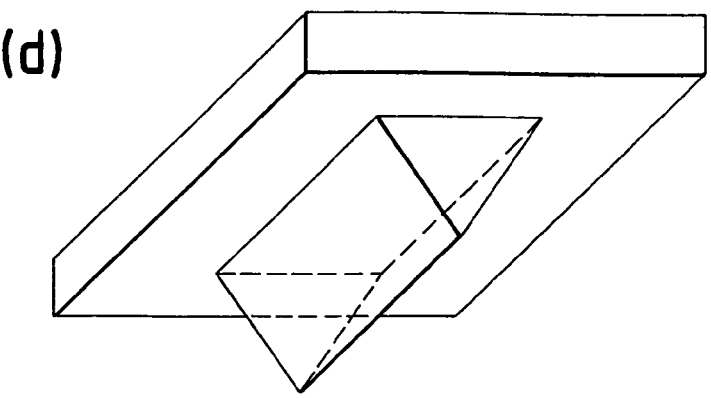

FIG. 3 shows a sensor in accordance with the invention in the manner of a depletion layer field effect transistor (JFET) of the depletion type. In contrast to the known sensors, for example shown in FIGS. 1 and 2, the sensor surface 12 of the sensor of the invention is made three-dimensional and preferably formed as a peak, at least regionally. A non-exclusive selection of designs of a three-dimensional sensor surface 12 which can be considered in accordance with the invention is shown by way of example in FIG. 4: Thus the sensor surface 12 can for example be formed (a) as a 3- or 4-sided pyramid peak or (b) as a conical peak. Conceivable is also (c) a stair-like or (d) wedge-like design of the peak. In addition the three-dimensional design of the substrate surface 12 in accordance with the invention also includes spherical shapes.

The sensor surface 12 of the sensor in FIG. 3 is formed at least regionally as a peak of a pyramid. A structure of this kind can be easily manufactured by known etching or sawing processes in substrates, in particular from crystalline silicon.

The substrate 10 of the sensor consists of p-doped silicon whereas the drain 14 and source 16 are formed as n-doped regions in the substrate 10. In this connection drain 14 and source 16 are arranged in the planar region 32 of the sensor surface 12 at the base of the pyramid and extend in a region close to the surface along a large part of the pyramid flanks 34 in the direction of the pyramid peak 36. The region of the pyramid peak 36 close to the surface is itself formed as the channel 26. In this connection it can, as already mentioned above, be an inverted or doped channel so that a sensor of the type of an FET of the enhancement type or—as in the illustrated embodiment—of the depletion type is present.

A voltage can be applied by means of a voltage source 20 between source 14 and drain 16 by means of a drain electrode 18 applied to the drain 14 and also a source electrode 22 applied to the source 16 and a current flowing through the channel 26 between source 16 and drain 14 can be measured by means of a current measuring device 38. In this arrangement the electrical resistance of the channel 26 can be preset by a voltage which can be applied to the substrate 10 by means of a setting electrode 28 attached to the substrate 10.

If the sensor, i.e. the pyramid tip 36, is now brought into the vicinity of or into contact with the sample surface 40 of a sample 42 to be investigated and a voltage applied between sensor and probe 42 by means of a a voltage source 44, then an electrical field is produced between sample surface 40 and pyramid tip 36 which acts on the channel 26 and changes its conductivity. The strength of the electrical field between sample surface and pyramid tip 36 can be determined by the current flow between drain 14 and source 16 determined by the measurement device 38 and permits conclusions to be drawn on the nature of the sample surface 40.

The lateral resolution capability of the sensor is on the one hand dependent on the spacing of the pyramid tip 36 from the sample surface 40. In this connection a minimum spacing is preset by the thickness of the oxide layer 24 which covers the sensor surface 12.

On the other hand, the resolution capability depends on the lateral extent of the channel 26. Since the channel 26 is, in accordance with the invention, disposed over the apex of the pyramid tip 36 the effective dimension of the channel 26 is smaller than the actual dimension of the channel 26 because of the quadratic dependency of the electrical field strength on the spacing from the sample surface 40. The resolution capability of the sensor is higher the more steeply the pyramid is formed, i.e. the smaller the angle which the flanks 34 of the pyramid form with one another.

A sensor in accordance with the invention can be integrated for example into the tip of a scanning probe of a scanning probe microscope and moved in a scanning movement relative to a sample surface whereby an investigation of a sample surface is made possible with a high spatial resolution.

In this connection the sensor can for example be removed at a constant height Z with respect to an XY plane defined at least approximately by the sample surface 40 over the sample surface 40, with the current flow through the transistor being recorded in dependence on the position of the sensor. Alternatively the sensor can be moved following the contour of the sample surface across the sample surface 40 in such a way that the current flow through the transistor always remains constant, with the deflection of the sensor in the Z direction being recorded in dependence on the XY-position of the sensor. In both cases a spatially resolved image of the sample surface 40 can be produced which permits conclusions on the nature of the sample 42 or sample surface 40.

Since probes with tip geometry are also used in scanning force microscopy, a sensor in accordance with the invention can be used additionally or simultaneously also for a probe of a conventional scanning force microscope.

In sensors which are based on the principle of the field effect transistor of the depletion type the effective width and depth of the channel 26 can be reduced by the application of a blocking voltage to the semiconductor substrate 10 and thus both the sensitivity and also the lateral resolution of this sensor can be increased beyond the level preset by the lithographic structuring. Through the combination of the JFET principle with a depletion type FET a plurality of highly resolving sensors can be realized which are based on a change of the channel resistance through interaction with the sample 42 to be investigated:

1. Detectors for electrical fields which exist between a solid body surface to be investigated and the sensor, with the field strength resulting from the electrical potential applied to the sample to be investigated, from the dielectric constant of an insulating material present on the sample surface and from the sample spacing from the sensor.
2. Detectors for electrical charges, in particular electrically charged molecules or atoms (ions) which are present in the vicinity of the sensor in the gas phase, in solution or absorbed on a surface of a solid body.
3. Chemical sensors through which the selective accumulation of chemical species (for example ions or molecules) can be detected at a correspondingly prepared gate electrode. Through the accumulation the potential of the gate electrode can be shifted (for example by a change of the work function of the electrode material) which has the consequence of a measurable change of the channel resistance. Either the gate electrode itself (for example palladium for hydrogen) or other mainly organic materials which selectively bind the species to be detected serve as the chemically selective materials. The selective material is in this connection located either between the gate electrode and the oxide layer which covers the channel (see for example U.S. Pat. No. 4,698,657) or is directly applied to the gate electrode, for example as a self organizing thin film (self assembled monolayer) (see for example U.S. Pat. No. 4,881,109).

In a chemical sensor without gate electrode the electrical field across the FET channel can also be produced by an electrolyte solution which is in direct contact with the oxide layer covering the channel by means of an ion selective membrane (see P. Bergveld, IEEE Transactions of Biomedical Engineering; Vol. 19; pages 342 and sequel (1972) and K. D. Wise et al., IEEE Transactions of Biomedical Engineering; Vol. 21, pages 458 and sequel (1974)).

In contrast to the different types of embodiment of chemical FET sensors cited the chemical detection by means of FET sensors in depletion operation and in particular in combination with a depletion layer operation (JFET effect) is provided in accordance with the invention.

4. High resolution temperature sensors for scanning probe microscopy in which the effect is exploited that the resistance of the channel changes with the temperature.

Basically the use of sensors in accordance with the invention is not restricted to probe tips but can rather be provided everywhere where the increase of the resolution in one dimension already represents an improvement and/or where the second dimension is determined by other lithographic methods. As an example the use as a chemical detector in a microstructure transport channel (microfluidic channel) should be named, for the specific or non-specific detection of chemical species flowing past in accordance with the above-named points 2 and 3 is named. A further example is the use as an electrostatic scanning sensor ("read head") for electrical charges stored in mass memories, in analogy to a magnetic read head of customary hard disk drives.

Figure 5:
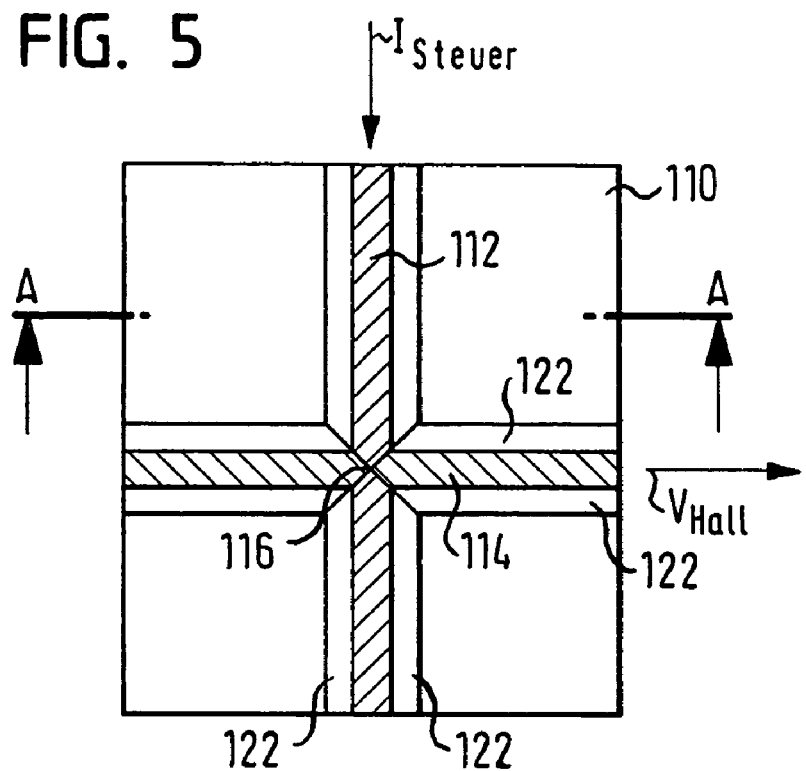
FIG. 5 is a plan view of a Hall sensor in accordance with the invention.

A further subject of the invention is the Hall sensor as shown in FIG. 5 for the detection of magnetic fields in accordance with the Hall effect principle. The Hall sensor of the invention has a p-conductive silicon substrate, with two n-conducting channels 112, 114 being provided in its surface-near region, with the two channels extending at right angles to one another and crossing in a crossing region 116. By applying a voltage a constant control current $I_{Steuer}$ can flow through one channel 112 with Hall voltage $V_{Hall}$ produced by an external magnetic field being able to be measured at the other channel 114.

The channels 112, 114 each form a pn junction with the substrate 110 with the regions 122 characterizing the respective space charge or depletion zones.

Figure 6:
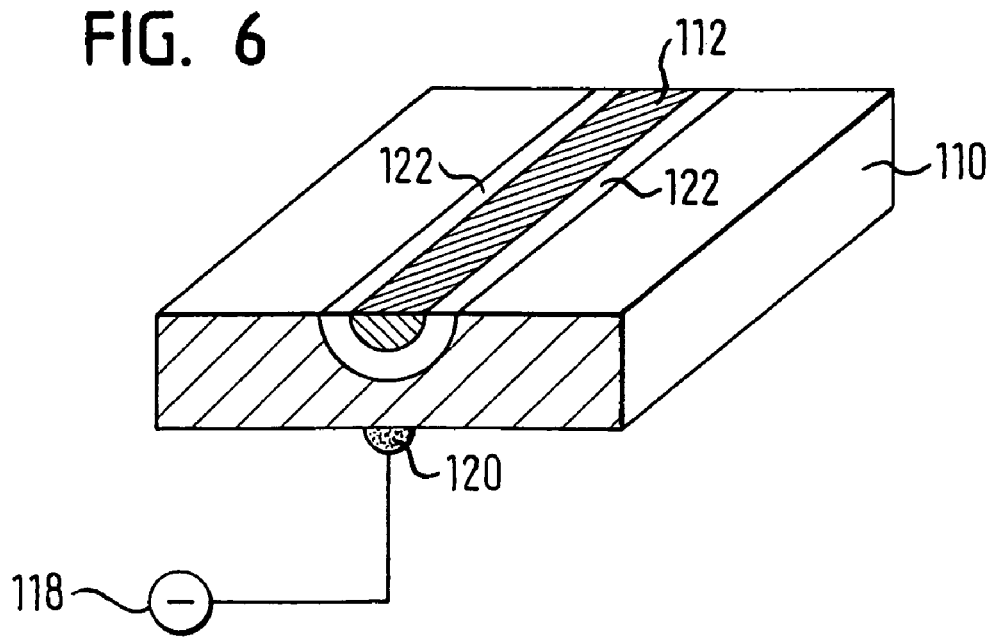
FIG. 6 a sectional view of the Hall sensor along the line A-A of FIG. 5.

As shown in FIG. 6 an electrode 120 connected to a voltage source 118 is attached to the substrate 110. By applying a voltage between the channels 112, 114 and the substrate 110 the extent of the channels 112, 114 can be changed, for the example reduced by depletion of charge carriers when the voltage is applied in the blocking direction of the pn junctions. In this manner the crossing region 116 can in particular be made smaller. This in turn results in an improvement of the resolution capability of the Hall sensor.

Figure 7:
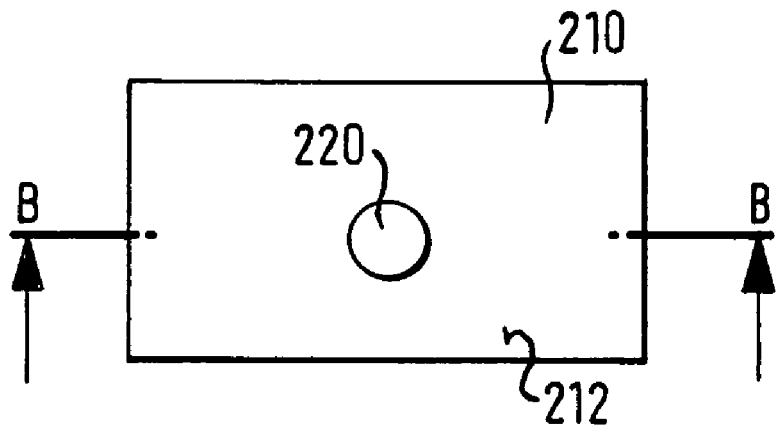
FIG. 7 a plan view of a semiconductor electrode in accordance with the invention.
Figure 8:
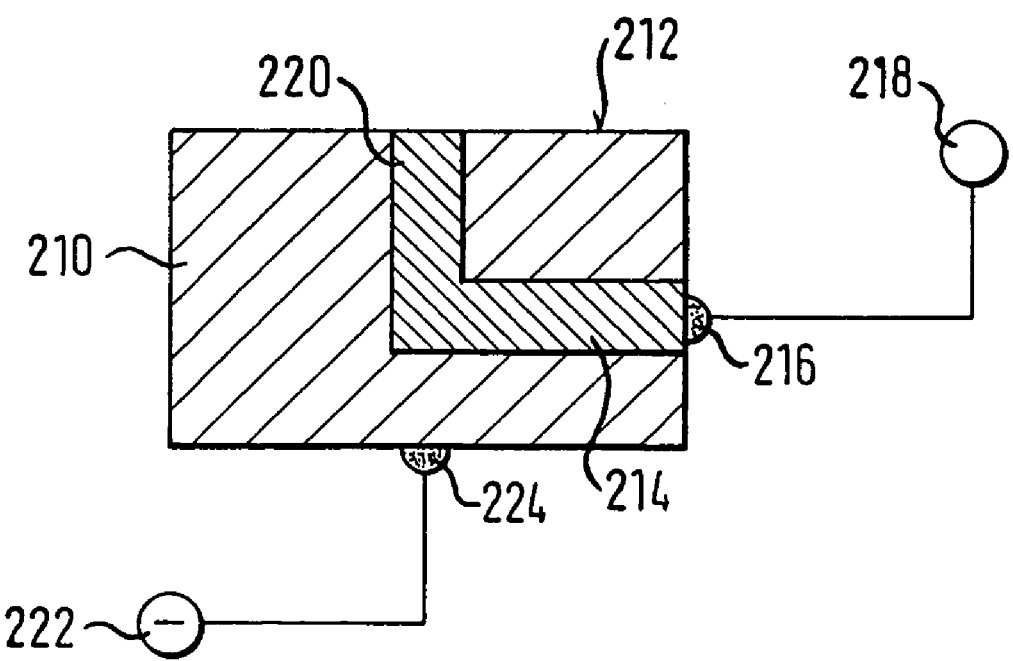
FIG. 8 a sectional view of the semiconductor electrode along the line B-B of FIG. 7.

A further subject of the invention is the semiconductor electrode shown in FIG. 7 the electrode area of which can be set in accordance with the invention following the JFET principle. The semiconductor electrode has a p-conducting silicon substrate 210 in which an n-conducting channel section 214 is formed beneath a substrate surface 212 and extends substantially parallel to the surface 212. At its one end this channel section 214 is connected by means of an electrode 216 to a current or voltage source 218. At the other end of the parallel extending channel section 214 a channel section 220 follows which extends perpendicular to the surface 212 and extends up to the surface 12, with the extent of the channel 220 at the surface 212 defining the electrode area.

An electrode 224 which is connected to a voltage source 222 is also attached to the substrate 210 for the application of a blocking voltage. By the application of a blocking voltage between the substrate 210 and the n-doped region 214, 220 the extent of the perpendicular channel section 220 at the substrate surface 212 can be controlled. In this manner, in a semiconductor electrode in accordance with the invention, an electrically settable electrode area can be achieved the size of which is less than the electrode area preset lithographically.

The semiconductor electrode in accordance with the invention can as a consequence be used as a detection means with an electrically settable lateral resolution, with the electrically set resolution exceeding the lithographically preset resolution. In addition, since the perpendicularly extending channel section 220 is surrounded by the opposite electrical potential of the substrate a concentration of the field strength in the direction perpendicular to the substrate surface 212 results and leads to a focusing effect which contributes to a further increase of the resolution.

A semiconductor electrode in accordance with the invention can for example be used as a highly spatially resolving probe for capacity measurements or as an electrochemical probe for the determination of the electrochemical potential of an electrolyte solution. In this connection the semiconductor electrode can be integrated in accordance with the invention into the tip of a probe of a scanning probe microscope and can be used for the capacity measurement or for the electrochemical determination of the potential. In conjunction with metal electrodes both microscope types are used and are referred to as "Scanning Capacitance Microscopy" (SCM) and "Scanning Electrochemical Microscopy" (SECM).

The invention claimed is:

1. A sensor for the investigation of sample surfaces or fields adjacent to the sensor, the sensor comprising at least one field effect transistor (FET) formed in a substrate comprising at least one semiconductor material and having source and drain regions defined in said substrate and being of the opposite conductivity type from said substrate, the substrate including a three-dimensional projecting region with a tip region, a channel region defined in at least the tip region of said three-dimensional projecting region and extending between said source and drain regions, and an electrode for the application of a setting voltage in order to electrically pre-set an electrical resistance of said channel region, said field effect transistor being adapted by said channel region in said tip region of said three-dimensionally projecting region to cooperate with at least one of a field, a charge and a sample disposed in the proximity of said tip region external of the tip region and acting as an external gate.

2. A sensor according to claim 1, wherein the sensor comprises a probe for a scanning probe microscope.

3. A sensor in accordance with claim 1, the three-dimensional projecting region being of pyramid-like shape in the region of said channel.

4. A sensor in accordance with claim 1, the three-dimensional projecting region being of conical shape in the region of said channel.

5. A sensor in accordance with claim 1, the three-dimensional projecting region being of step-like shape in the region of said channel.

6. A sensor in accordance with claim 1, the three-dimensional projecting region being of wedge-like shape in the region of said channel.

7. A sensor in accordance with claim 1, said field effect transistor (FET) being a field effect transistor of the enhancement type (enhancement mode FET).

8. A sensor in accordance with claim 1, said field effect transistor(FET) being a field effect transistor of the depletion type (depletion mode FET).

9. A sensor in accordance with claim 1, said field effect transistor (FET) being layer field effect transistor (junction effect transistor JET).

\* \* \* \* \*